(12) United States Patent
Grunhut et al.

(10) Patent No.: US 8,979,807 B2
(45) Date of Patent: Mar. 17, 2015

(54) AUTOMATIC INJECTION DEVICE WITH AUDIBLE INDICATOR OF COMPLETED INJECTION

(75) Inventors: Guillaume Grunhut, Grenoble (FR); Frederic Perot, Saint Paul de Varces (FR); Samuel Gagnieux, Bresson (FR); Romain Lanier, Grenoble (FR); Yves Enfoux, Varces Alliere et Risset (FR)

(73) Assignee: Becton Dickinson France, Le Ponte de Claix (FR)

( * ) Notice: Subject to any disclaimer, the term of this patent is extended or adjusted under 35 U.S.C. 154(b) by 968 days.

(21) Appl. No.: 13/121,201

(22) PCT Filed: Sep. 29, 2008

(86) PCT No.: PCT/IB2008/003285
§ 371 (c)(1),
(2), (4) Date: May 25, 2011

(87) PCT Pub. No.: WO2010/035059
PCT Pub. Date: Apr. 1, 2010

(65) Prior Publication Data
US 2011/0218500 A1 Sep. 8, 2011

(51) Int. Cl.
*A61M 5/315* (2006.01)
*A61M 5/20* (2006.01)

(52) U.S. Cl.
CPC .......... *A61M 5/2033* (2013.01); *A61M 5/31511* (2013.01); *A61M 5/3157* (2013.01); *A61M 2005/206* (2013.01); *A61M 2205/581* (2013.01)
USPC ........................................ 604/228

(58) Field of Classification Search
CPC ................ A61M 2005/206; A61M 2205/581; A61M 5/2033; A61M 5/31511; A61M 5/3157; A61M 5/3287
USPC ................. 604/135–137, 181, 187, 208–210, 604/218–231, 191, 192, 198
See application file for complete search history.

(56) References Cited

U.S. PATENT DOCUMENTS

| | | | |
|---|---|---|---|
| 5,599,309 A | 2/1997 | Marshall et al. | |
| 5,779,677 A | 7/1998 | Frezza | |
| 5,957,896 A | 9/1999 | Bendek | |
| 6,086,566 A | 7/2000 | Arnissolle | |
| 7,976,499 B2 | 7/2011 | Grunhut et al. | |
| 2004/0054326 A1 | 3/2004 | Hommann et al. | |
| 2006/0264830 A1 | 11/2006 | Hommann | |
| 2008/0228143 A1 | 9/2008 | Stamp | |
| 2008/0228147 A1 | 9/2008 | David-Hegerich et al. | |
| 2008/0262438 A1* | 10/2008 | Bollenbach et al. | 604/207 |

FOREIGN PATENT DOCUMENTS

| | | |
|---|---|---|
| DE | 198 19 409 A1 | 11/1999 |
| DE | 100 15 616 A1 | 10/2001 |

(Continued)

*Primary Examiner* — Kami A Bosworth
*Assistant Examiner* — Imani Hayman
(74) *Attorney, Agent, or Firm* — Hoffmann & Baron, LLP (57) ABSTRACT

The present invention relates to a device for automatic injection including a container, a piston and a piston rod coupled to the piston during the injection. A biasing element is provided for causing distal movement of the piston rod with respect to the container, with a housing receiving the container, the piston rod and the biasing element. The device further including a controlling arrangement for producing an audible indicator at the end of injection.

5 Claims, 4 Drawing Sheets (56) References Cited

FOREIGN PATENT DOCUMENTS

| DE | 10 2004 052 219 A1 | 5/2006 |
|----|---------------------|--------|
| DE | 10 2007 013 838 A1 | 9/2008 |
| EP | 0 897 728 A1 | 2/1999 |
| EP | 1 208 859 A1 | 5/2002 |
| WO | 00/24441 A1 | 5/2000 |
| WO | 2005/070481 A1 | 8/2005 |
| WO | 2006/052737 A1 | 5/2006 |
| WO | 2007/132353 A2 | 11/2007 |

* cited by examiner

AUTOMATIC INJECTION DEVICE WITH AUDIBLE INDICATOR OF COMPLETED INJECTION

The present invention relates to a device for automatic injection of a product ensuring the user that the product has been substantially completely injected.

In the present application, the distal end of a component or of a device is to be understood as meaning the end furthest from the user's hand during proper use and the proximal end is to be understood as meaning the end closest to the user's hand during proper use. Likewise, in the present application, "the distal direction" is intended for defining the direction of the injection, and the "proximal direction" for defining the opposite direction to the direction of injection.

Some illnesses necessitate regular injections for drugs or products, for instance on a daily basis. In order to simplify the treatment of such illnesses, some devices for automatic injection have been developed to allow the patient to perform the injection on its own.

Of course, since the patient is usually neither a nurse nor an educated person in medical devices, such devices for automatic injection must prove to be very simple to use and very safe. In particular, it is important to ensure that a controlled dose of a product is injected with such a device, that is to say a complete injection must be performed. Moreover, in some cases, the user may withdraw the device for automatic injection before the injection is completed. It is therefore important for the user to be informed that the product has been substantially completely injected and that he may withdraw the device from the injection site.

It is known from the patent application WO 2007/132353 an automatic injection device wherein a sound is emitted throughout the injection, thereby indicating the patient that the injection is completed when the sound ceases.

There is a need for self-injection devices that would clearly indicate to the user that the injection is completed.

The present invention meets this need by proposing an alternative to the previously described device. The present invention proposes a device for automatic injection of a product into an injection site, said device producing an audible indicator when the injection is completed.

The present invention relates to a device for automatic injection of a product into an injection site, the product being carried by a container having an open proximal end and a substantially closed distal end carrying a needle to provide an outlet port for the product from the container, and a piston provided in the container and distally movable with respect to the container, the distal movement of the piston causing the product to be expelled from the container through the needle thereby realising the injection of said product, said device comprising:

a piston rod intended to be coupled to said piston in the distal direction during the injection, biasing means for causing distal movement of said piston rod with respect to said container during the injection, a housing designed for receiving at least partially said container, said piston rod and said biasing means, controlling means designed for producing an audible indicator when said piston is near said distal end of the container and the product is substantially completely expelled from the container thereby providing an indication to a user that injection of the product is completed, said device being characterized in that:

said controlling means comprise at least one first element, being flexible or breakable and directly or indirectly coupled to said housing or to said piston rod, during the injection, and at least one second element, said second element being coupled directly or indirectly to said piston rod or to said housing, during the injection, said first and second elements cooperating with each other at the end of injection under the effect of the said biasing means so as to produce said audible indicator.

The device of the invention allows the user to be clearly informed of the end of injection.

In the present application, by the expression "A is coupled to B in direction X" is meant that A is attached to B when A is caused to move in the X direction: in other words, if A is caused to move in the X direction, then B is also caused to moved in the X direction, drawn by A.

In the present application, by the expression "A is coupled directly or indirectly to B" is meant that A and B are fixed with respect to each other, either by A being directly attached to B or by A being attached to B via an intermediate piece linking A to B (indirect coupling).

In an embodiment of the invention, said first element is distinct from said biasing means.

In an embodiment of the invention, said first element comprises at least one radially flexible part, capable of being deflected from a stressed position to a free position, said radially flexible part producing a sound when going from its stressed position to its free position, said second element comprising at least an abutment surface, said abutment surface putting a strain on said radially flexible part so as to put it in its stressed position before the end of injection, and said abutment surface being caused to release said strain at the end of injection under the effect of the biasing means.

For example, at the end of injection, under the force exerted by the biasing means upon the radial flexible part or on the abutment surface, said radial flexible part, respectively said abutment surface, escapes said abutment surface, respectively said radially flexible part, the friction of said part on said surface producing a sound. In embodiments, an additional sound may be produced, for example by said radially flexible part hitting a contact surface when returning to its free position, thereby producing an additional sound.

In an embodiment of the invention, said piston rod comprising a hollow cylinder provided with a collar at its proximal end, the wall of said collar being outwardly radially flexible, and said device further comprising a longitudinal rod fixed with respect to said housing during the injection, said longitudinal rod being proximally spaced with respect to said piston rod, a distal end of said longitudinal rod being slidingly received within said hollow cylinder and being provided with a projection having an external diameter greater than the internal diameter of said collar, said flexible radially part comprises said wall of said collar and said abutment surface comprises said projection, said projection putting a strain on the wall of said collar before the end of injection, and releasing said strain at the end of injection by escaping said collar under the effect of said biasing means.

In such an embodiment, the friction of the projection on the collar produces a sound, at the time said projection escapes the collar under the force exerted by the biasing means. The user is therefore informed that the injection is completed.

In another embodiment of the invention, said radially flexible part comprises at least one longitudinal flexible leg having a proximal end fixed to said housing and a free distal end, said abutment surface comprises an outer wall of said piston rod, said outer wall of said piston rod being in contact with, and putting a strain on, the distal end of said longitudinal flexible leg before the end of injection so as to deflect it in its stressed position, said outer wall of said piston rod releasing said strain at the end of injection by escaping said longitudinal flexible leg under the effect of said biasing means.

In another embodiment of the invention, said radially flexible part comprises at least one longitudinal flexible leg, said longitudinal flexible leg having a distal end fixed on an outer wall of said piston rod, said abutment surface comprises a longitudinal projection of an inner wall of said housing, said longitudinal projection being in contact with, and putting a strain on the proximal end of said longitudinal flexible leg before the end of injection so as to deflect it in its stressed position, said longitudinal projection releasing said strain at the end of injection, by escaping said longitudinal flexible leg under the effect of said biasing means.

The device of the invention may further comprise a contact surface located on an inner wall of said housing, said longitudinal flexible leg hitting said contact surface when returning to its free position, thereby producing a sound.

In another embodiment of the invention, said first element comprises a breakable part, said breakable part having a proximal end directly or indirectly coupled to said housing, and a distal end directly or indirectly coupled to said piston rod, said breakable part being caused to break at the end of injection, under the effect of the biasing means, thereby producing said audible indicator.

In an embodiment of the invention, said breakable part comprises a deformable wire having a proximal end and a distal end, the proximal end of said deformable wire being fixed to a fixation point located in the proximal region of said housing, said fixation point being fixed with respect to said housing during injection, and the distal end of said deformable wire being fixed to a proximal end of said piston rod, the length of said deformable wire being less than the distance separating said proximal end of said piston rod from said fixation point at the end of injection, the distal movement of said piston rod under the effect of said biasing means causing said deformable wire to break at the end of injection. For example, said wire may be made of nylon, polypropylene, or other rigid or semi-rigid yet breakable material.

In another embodiment of the invention, said piston rod comprising a hollow cylinder provided with a collar at its proximal end, said breakable part comprises a rigid cable having a proximal end and a distal end, the proximal end of said rigid cable being fixed to a fixation point located in the proximal region of said housing, said fixation point being fixed with respect to said housing during injection, and the distal end of said rigid cable being slidingly received within said hollow cylinder, said distal end of said rigid cable being provided with a projection having an external diameter greater than the internal diameter of said collar, the length of said rigid cable being less than the distance separating said collar of said piston rod from said fixation point at the end of injection, the distal movement of said piston rod under the effect of said biasing means causes said rigid cable to break at the end of injection. For example, said rigid cable may be made of polypropylene or other breakable material.

The device of the present invention will now be further described in reference to the following description and attached drawings in which.

Figure 1:
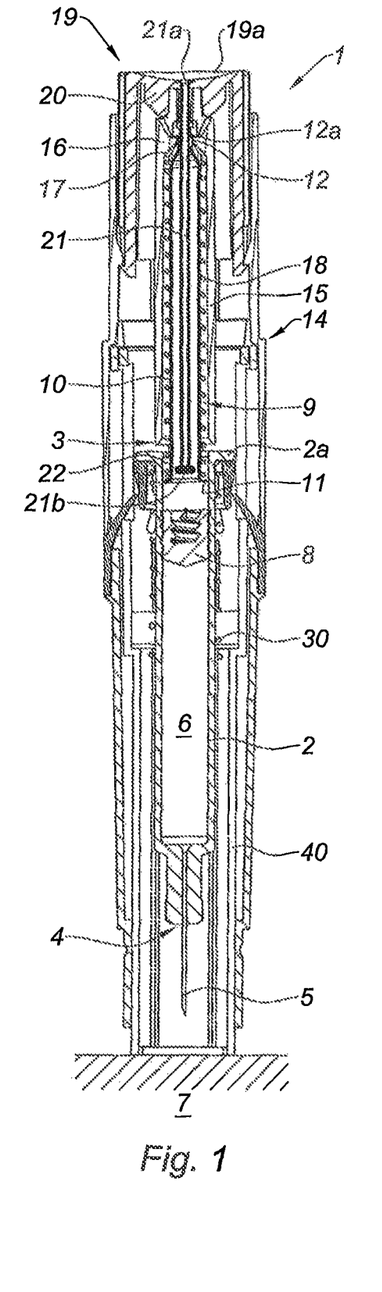
FIG. 1 is a longitudinal cross section view of a first embodiment of the device of the invention, before use.

Referring now to the drawings, the present invention will now be described in detail. FIG. 1 shows a longitudinal cross section of a first embodiment of the device for automatic injection according to the present invention, as provided to the user before use, and which is referred to as device 1 in the following description. The device 1 comprises a container 2 having a proximal open-end 3, a substantially closed distal end 4 bearing a needle 5; the container 2 carries a product 6 to be injected at an injection site 7. The container 2 is provided with an outer flange 2a at its proximal end. A piston 8 is provided in the container 2 and is movable with respect to said container 2. As it will appear in the description below, the movement of the piston 8 in the distal direction is intended to cause the product 6 to be expelled from the container 2. The device 1 comprises also a piston rod 9: as will appear from the description below, the piston rod 9 is intended to be coupled to the piston 8 in the distal direction during the injection.

Figure 2:
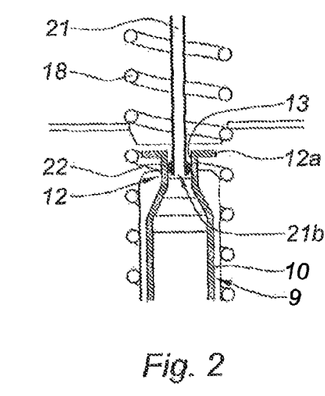
FIG. 2 is a partial cross section view of the device of FIG. 1 showing the position of the controlling means before the end of injection.
Figure 3:
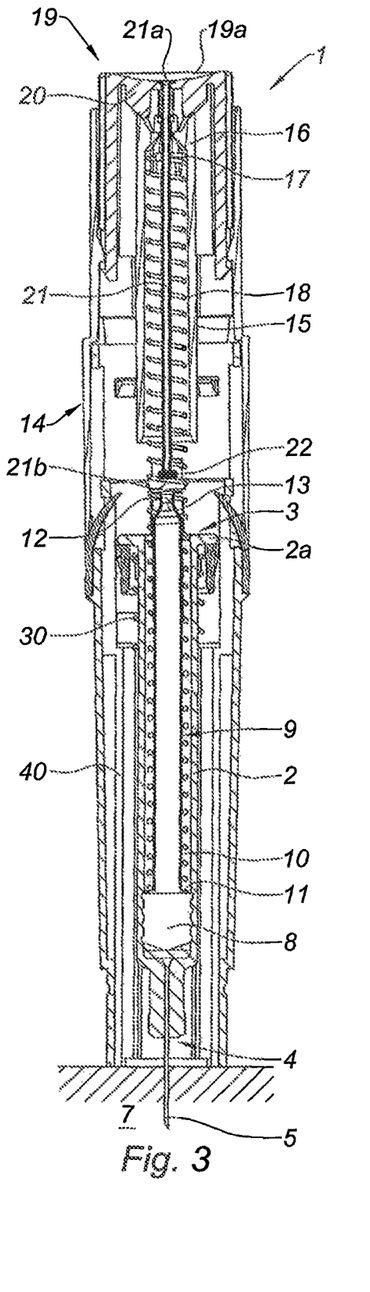
FIG. 3 is a longitudinal cross section view of the device of FIG. 1 at the end of the injection.

The piston rod 9, in the example shown on FIGS. 1-3, comprises a hollow cylinder 10 provided with a flange 11 at its distal end and with a collar 12 at its proximal end, the inner diameter of said collar 12 being less than the inner diameter of said hollow cylinder 10. The collar 12 is provided at its proximal end with an outer flange 12a. The wall 13 of the collar 12 is outwardly radially flexible, that is to say, the inner diameter of the collar 12 is capable of expanding slightly under the effect of a strain applied on the perimeter of the inner face of the wall 13 of said collar 12 in the centrifugal direction.

The device 1 further comprises a housing 14: the housing 14 has the global shape of a tube open at both ends. The housing 14 receives the container 2 and the piston rod 9. As will appear from the description below, the container 2 is fixed with respect to the housing 14 during the injection phase. The container 2 may be fixed to the housing 14 during the injection phase by any coupling or fixation means such as clips, cooperating parts engaged with each other: such coupling and/or fixation means are described in WO2007/132353 and will not be repeated herein.

The housing 14 comprises in its proximal region an inner cylinder 15 provided with a rim 16 forming a distal abutment surface 17.

The device of FIGS. 1-3 further comprises biasing means for automatically pushing the piston rod 9 distally at the time of injection. In the example shown, these biasing means are under the form of a helical spring 18 located around the piston rod 9. The proximal end of the helical spring 18 bears on the distal abutment surface 17 of the rim 16 of the inner cylinder 16 of the housing 14, and the distal end of said helical spring 18 bears on the proximal face of the flange 11 of the proximal end of the piston rod 9.

In the before use position as shown on FIG. 1, the helical spring 18 is in a compressed position and the outer flange 12a of the collar 12 of the piston rod 9 bears on a proximal abutment surface of two flexible teeth (not shown) located on the inner cylinder 15 of the housing 14.

On the embodiment shown on FIGS. 1-3, the device 1 further comprises a push button 19 for activating the injection. On the example shown, the push button 19 is located within the proximal region of the housing 14 and is capable of being moved slightly in the distal direction under pressure exerted by the user on a proximal transversal wall 19a of said push button 19. To this effect, the push button 19 is provided on the inner face of its proximal transversal wall 19a with two teeth 20 extending in the distal direction. At the time of activation of the injection, these two teeth 20 are intended to come into contact with and deflect the two flexible teeth (not shown) of the inner cylinder 15 on which bears the outer flange 12a of the piston rod 9, in order to free said piston rod 9 from said cylinder 15. The push button 19 acts then as triggering means of the injection.

The push button 19 is further provided with a longitudinal rod 21, having a proximal end 21a attached to the inner face of the transversal proximal wall 19a of the push button 19, and a free distal end 21b. The outer diameter of the longitudinal rod 21 is less than the inner diameter of the hollow cylinder 10 of the piston rod 9. The longitudinal rod 21 is proximally spaced with respect to the piston rod 9 and its distal end 21b slidingly received within the hollow cylinder 10 of the piston rod 9, as shown on FIG. 1.

The distal end 21b of the longitudinal rod 21 is provided with a projection 22 having an outer diameter less than the inner diameter of the hollow cylinder 10 but greater than the inner diameter of the collar 12.

The functioning of the device of FIGS. 1-3 will now be explained.

The user is provided with the device 1 in the before use position as shown on FIG. 1. In this position, as mentioned before, the helical spring 18 is in a compressed position. In this position also, the longitudinal rod 21 is received within the hollow cylinder 10 of the piston rod 9.

When the user decides to proceed to the injection of the product, he applies the device 1 on the injection site 7 and triggers the injection by exerting a distal pressure on the transversal proximal wall 19a of the push button 19. The push button 19 is thereby caused to move distally with respect to the housing 14 and, as already mentioned above, the teeth 20 free the piston rod 9 from the inner cylinder 15, thereby freeing the helical spring 18 which is caused to expand distally in order to come back to its natural extended position. Such an activation step for freeing biasing means, such as the helical spring 18 of the device 1 of the present invention, is described in WO2007/132353.

As the helical spring 18 expands in the distal direction, it pushes the piston rod 9 distally, by means of its distal end bearing on the flange 11 of the piston rod 9. As a consequence of its distal movement, the piston rod 9 comes in contact with the piston 8 and couples with the container 2, causing a limited distal movement of the container 2 and insertion of the needle 5 in the injection site 7 (as shown on FIG. 3): such an insertion step is described for example in WO2007/132353. The container 2 is then stopped from further moving distally, by means of its outer flange 2a coming in abutment, via an intermediate spring 30, against a needle shield 40 received in the distal region of the housing 14 and coupled to said housing 14 via classic means, for example described in WO2007/132353. As shown on FIG. 3, the distal end of the needle shield 40 is in abutment on the injection site 7. As a consequence, the further distal movement of the piston rod 9 causes the piston 8 to move distally: the injection steps begins. The piston rod 9 is therefore coupled to the piston 8 in the distal direction.

During the insertion and injection step, the push button 19 remains fixed with respect to the housing 14, for example by means of coupling means or fixation means (not shown). The longitudinal rod 21 is therefore fixed with respect to the housing during the injection. As a consequence, when the piston rod 9 moves distally in order to realize the insertion and injection steps, the longitudinal rod 21 is caused to slide with respect to the hollow cylinder 10 of said piston rod 9.

On FIG. 2 is shown the relative positions of the piston rod 9 and of the longitudinal rod 21 with respect to each other right before the end of injection. As appears clearly from this figure, the projection 22 of the distal end 21b of the longitudinal rod 21 comes in contact with the inner face of wall 13 of the collar 12 of the hollow cylinder 10 of the piston rod 9. The wall 13 of the collar 12 being radially flexible and the outer diameter of the projection 22 being greater than the inner diameter of the collar 12, said wall 13 of said collar 12 is caused to deflect radially outwardly: in other words, under the effect of the strain put on the inner face of the wall 13 of the collar 12 by the projection 22 which acts as an abutment surface, the inner diameter of the collar 12 is caused to expand slightly.

The FIG. 3 shows the relative positions of the collar 12 of the piston rod 9 and of the projection 22 of the longitudinal rod 21 once the piston rod 9 has been caused to move further distally and right at the end of injection. Under the effect of the force of the helical spring 18, the projection 22 has escaped the collar 12 which has come back to its free position: the friction of the projection 22 on the wall 13 of the collar 12 as said projection escapes said collar 12 produces a sound which acts as an audible indicator for the user that the injection is completed. As can be seen from this FIG. 3, the piston 8 is now close to the distal end of the container 2 and the product is substantially completely expelled from the container 2.

In this example, the wall 13 of the collar 12 acts as a first flexible element located on the piston rod 9 and the projection 22 acts as a second element coupled to the housing, said first and second elements cooperating with each other under the effect of the biasing means 18 so as to produce the audible indicator.

Figure 4:
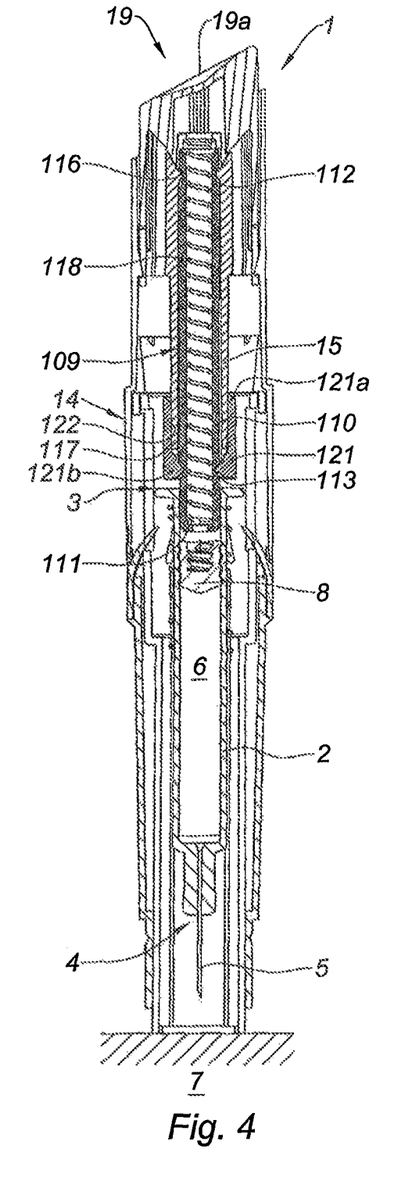
FIG. 4 is a longitudinal cross section view of second embodiment of the device of the invention, before use.
Figure 5:
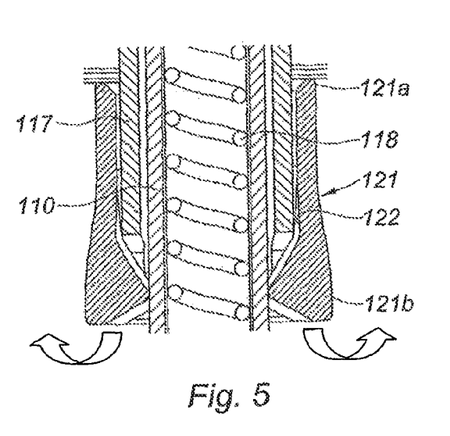
FIG. 5 is a partial cross section view of the device of FIG. 4 showing the position of the controlling means before the end of injection.
Figure 6:
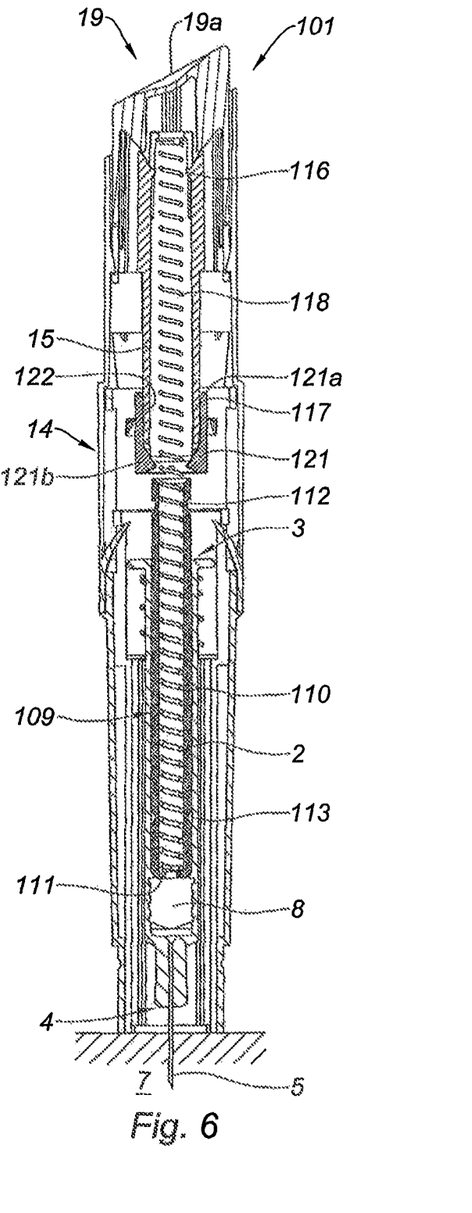
FIG. 6 is a longitudinal cross section view of the device of FIG. 4 at the end of the injection.

On FIGS. 4-6 is shown a second embodiment of the device of the invention, referred to as device 101, in which the first flexible element is coupled to the housing. On these figures, the references designating the same parts as in FIGS. 1-3 have been maintained.

The device 101 of FIGS. 4-6 comprises a piston rod 109 having the shape of a hollow cylinder 110 closed at its distal end by a transversal wall 111. In the embodiment of these figures, the biasing means are under the form of a helical spring 118 received within the hollow cylinder 110 of the piston rod 109. The distal end of the helical spring 118 bears on the proximal face of the transversal wall 111 of the piston rod 109 and the proximal end of the helical spring 118 bears on an abutment surface (not shown) located on the inner cylinder 15 of the housing 14 in a similar manner as described in FIGS. 1-3.

Before use, the piston rod 109 is coupled to the housing 14 by means of radial projections 116 of the inner cylinder 15 engaged in proximal recesses 112 provided in the proximal region of the outer wall of the piston rod 109.

The outer wall of the piston rod 109 is further provided with distal recesses 113, distally spaced with respect to said proximal recesses 112.

The device 101 further comprises two longitudinal flexible legs 121: the proximal ends 121a of the longitudinal flexible legs 121 are fixed to the housing 14 and the distal ends 121b of said longitudinal legs 121 are free. In the before use position, as shown on FIG. 4, the free distal ends 121b of the longitudinal flexible legs 121 abut in the distal recesses 113 of the outer wall of the piston rod 109. In this position, the longitudinal flexible legs 121 are in their free position and the inner wall 122 of each longitudinal flexible leg 121 is parallel to, and in soft contact with, a distal longitudinal wall 117 of the inner cylinder 15 of the housing 14, as shown on FIG. 4.

In order to proceed with the injection, the user pushes on the push button 19 in order to free the piston rod 109, in the same manner as described for FIGS. 1-3. As already described for the embodiment of FIGS. 1-3, the distal movement of the piston rod 109 causes the insertion of the needle 5 and the injection.

As described before, the push button 19 is fixed with respect to the housing 14 during injection.

During the injection phase, the piston rod 109 slides with respect to the longitudinal flexible legs 121 which are fixed with respect to the housing 14. As a consequence, the distal ends 121b of the longitudinal flexible legs 121 escape the distal recesses 113 and are therefore caused to deflect radially outwardly, due to the change of the outer diameter of the hollow cylinder 110 of the piston rod 109, as shown on FIG. 5. The outer wall of the piston rod 109 puts therefore a strain on the longitudinal flexible legs 121. As appears from this figure, in this stressed position of the longitudinal flexible legs 121, the inner walls 122 of said longitudinal flexible legs 121 are no more in contact with the distal longitudinal wall 117 of the inner cylinder 15.

When the piston 8 reaches the distal end of the container 2, as shown on FIG. 6, the piston rod 109, under the force of the helical spring 118 expanding, escapes from the longitudinal flexible legs 121. The outer wall of the piston rod 109 no longer applies a strain on the distal ends 121b of the longitudinal flexible legs 121 and the longitudinal flexible legs 121 come back in their free position, as shown on FIG. 6. By returning to their free position, the longitudinal flexible legs 121 hit the distal longitudinal wall 117 of the inner cylinder, especially via their distal ends 121b, thereby producing a sound and informing the user that the injection completed. The distal longitudinal wall 117 of the inner cylinder acts as a contact surface for the longitudinal flexible leg, on which they produce a sound.

Figure 7:
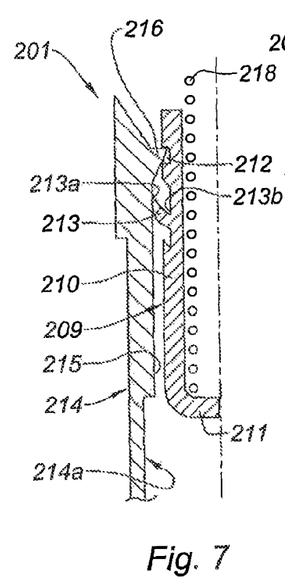
FIGS. 7-9 are partial cross section views of controlling means of a third embodiment of the device of the invention, respectively before use, during the injection before the end of injection, and at the end of injection.
Figure 8:
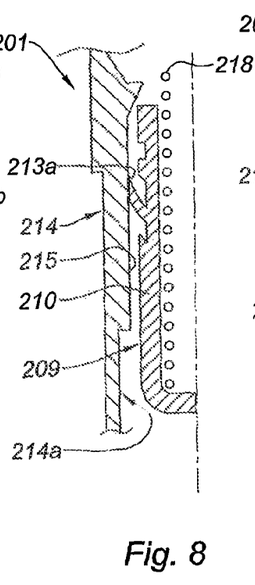

On FIGS. 7-8 are shown partial cross sections view of the cooperation of the first flexible element and of the second element of a third embodiment of the device of the invention.

The device 201 of FIGS. 7-8 comprises a piston rod 209 comprising a hollow cylinder 210 closed at its distal end by a transversal wall 211 and receiving the therein a helical spring 218 as biasing means. The piston rod 209 is provided on its outer wall with a proximal recess 212 and with a flexible longitudinal leg 213, distally spaced with respect to said proximal recess 212. The distal end 213b of the flexible longitudinal leg 213 is fixed to the outer wall of the piston rod 209 whereas its proximal end 213a is free. The device 201 further comprises a housing 214 comprising on its inner wall a longitudinal projection 215. The inner wall of the housing 14 is further provided with a radial tooth 216 proximally spaced from said longitudinal projection 215 and with a contact surface 214a distally spaced from said longitudinal projection 215.

As shown on FIG. 7, in the before use position of the device 201, the proximal end 213a of the flexible longitudinal tongue 213 abuts on the longitudinal projection 215 of the housing 214 and the radial tooth 216 is engaged in the proximal recess 212 of the outer wall of the piston rod 209.

At time of triggering the injection, the radial tooth 216 is disengaged from the proximal recess 212 (step not shown), and the piston rod 209 is freed and caused to move distally under the action of the freed helical spring 218. As shown on FIG. 8, during the injection phase, the piston rod 209 moves distally and the distal end 213a of the flexible longitudinal tongue 213 slides distally with respect to the longitudinal projection 215 of the housing 214. During this step, the longitudinal projection 215 applies a strain on the flexible longitudinal tongue 213 which is in its stressed position.

Figure 9:
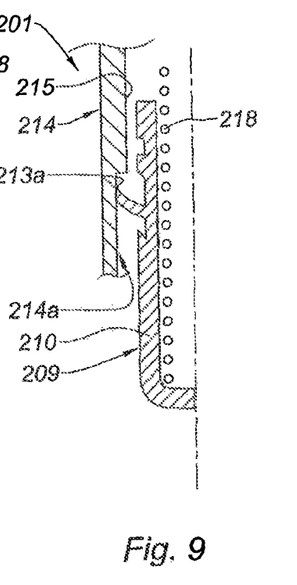

At the end of injection, as shown on FIG. 9, the distal end 213a of the flexible longitudinal tongue 213 reaches the distal end of the projection 215 and escapes said longitudinal projection 215, coming back to its non stressed position. By returning to its non stressed position, the distal end 213a of the flexible longitudinal tongue 213 hits the contact surface 214a of the inner wall of the housing 214, thereby producing a sound informing the user that the injection is completed.

Figure 10A:
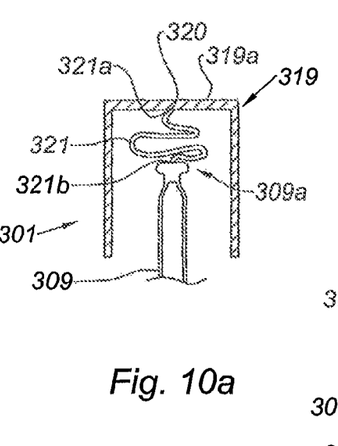
FIGS. 10a and 10b are partial cross section views of controlling means of a fourth embodiment of the device of the invention, respectively before use and at the end of injection.
Figures 10B, 11:
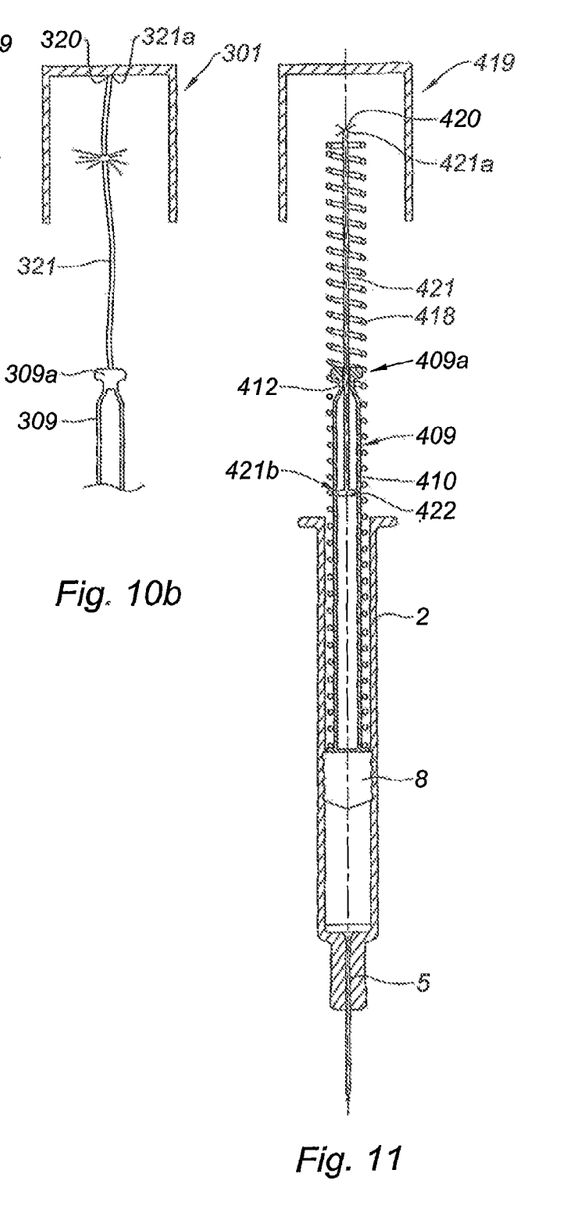
FIG. 11 is a partial cross section view of a fifth embodiment of the device of the invention during injection, before the end of injection.

On FIGS. 10a and 10b, is shown partially a fourth embodiment of the device of the invention, in which the first element is breakable. The device 301 of FIGS. 10a and 10b comprises a piston rod 309 at the proximal end 309a of which is fixed the distal end 321b of a wire 321. The proximal end 321a of the wire 321 is fixed at a fixation point 320 of the transversal wall 319a of a push button 319, coupled to the housing (not shown) during the injection phase. The fixation point 320 is therefore located in the proximal region of the housing 14 and is fixed with respect to said housing 14 during the injection. The wire 321 is deformable and is able to be folded on itself, as shown on FIG. 10a, in the before use position of the device 301.

The length of the wire 321 is less than the distance separating the fixation point 320 from the proximal end 309 of the piston rod 309 when the device 301 is in its end of injection position. As a consequence, when the piston (not shown) reaches the distal end of the container (not shown), the wire 321 unfolds until it breaks under the force of the helical spring (not shown) drawing the piston rod 309 in the distal direction, as shown on FIG. 10b.

When the wire 321 breaks, as shown on FIG. 10a, it produces a sound, thereby informing the user that the injection is completed.

The wire 321 may be made of any material capable of breaking under a strain. For example, the wire 321 is made of nylon, polypropylene, or other rigid or semi-rigid yet breakable material.

FIG. 11 shows partially a fifth embodiment of the device of the invention, in which the wire of FIGS. 10a and 10b is replaced by a rigid cable 421: the proximal end 421a of the rigid cable 421 is fixed at a fixation point 420 located on the push button 419, said push button 419 being coupled to the housing (not shown) during the injection phase. The rigid cable 421 is allowed to slide within a hollow cylinder 410 of the piston rod 410.

The distal end 421b of the rigid cable 421 is provided with a projection 422, the outer diameter of which is greater than the inner diameter of a collar 412 provided at the proximal end 409a of the hollow cylinder 410 of the piston rod 409. The wall of the collar 412 is not flexible and the inner diameter of the collar 412 is not allowed to expand under strain.

The length of the rigid cable 421 is less than the distance separating the fixation point 420 from the collar 412.

During the injection phase, the projection 422 is allowed to slide within the hollow cylinder 10 of the piston rod 409 until it comes in contact with the collar 412 just before the end of injection.

When the projection 422 comes in contact with the collar, it is not allowed to escape said collar 412, the wall of said collar 412 being not flexible. As a consequence, and under the force of the helical spring 418 causing the distal movement of the piston rod 309, the rigid cable is caused to break at the end of injection, thereby producing a sound and informing the user that the injection is completed.

The rigid cable 421 may be made of any material capable of breaking under a strain. For example, the rigid cable 421 is made of polypropylene or other breakable material.

The device of the invention allows the user to be clearly informed that the injection is completed. This is particularly important in self-injection devices where the injection is realized via automatic means such as biasing means, on which the user has no influence. The user being a patient, not used to injection devices in general, it is important that he be informed of the end of injection and of the time when the product is substantially completely expelled, so that he can safely withdraw the injection device from the injection site.

What is claimed is:

1. A device for automatic injection of a product into an injection site, the product being carried by a container having an open proximal end and a substantially closed distal end carrying a needle to provide an outlet port for the product from the container, and a piston provided in the container and distally movable with respect to the container, the distal movement of the piston causing the product to be expelled from the container through the needle thereby realizing the injection of said product, said device comprising:

a piston rod intended to be coupled to said piston in the distal direction during the injection, biasing means for causing distal movement of said piston rod (9; 109; 209; 309; 409) with respect to said container during the injection, a housing designed for receiving at least partially said container, said piston rod and said biasing means, and controlling means designed for producing an audible indicator when said piston is near said distan end of the container and the product is substantially completely expelled from the container thereby providing an indication to a user that injection of the product is completed, wherein, said controlling means comprise a breakable part having a proximal end directly or indirectly coupled to said housing, and a distal end directly or indirectly coupled to said piston rod, said breakable part being caused to break at the end of injection, under the effect of the biasing means, thereby producing said audible indicator.

2. A The device according to claim 1, wherein said breakable part comprises a deformable wire having a proximal end and a distal end, the proximal end of said deformable wire being fixed to a fixation point located in a proximal region of said housing, said fixation point being fixed with respect to said housing during injection, and the distal end of said deformable wire being fixed to a proximal end of said piston rod, the length of said deformable wire being less than the distance separating said proximal end of said piston rod from said fixation point at the end of injection, the distal movement of said piston rod under the effect of said biasing means causing said deformable wire to break at the end of injection.

3. The device according to claim 2, wherein said wire is made of nylon or polypropylene.

4. The device according to claim 1, wherein said piston rod comprises a hollow cylinder provided with a collar at a proximal end, said breakable part comprises a rigid cable having a proximal end and a distal end, the proximal end of said rigid cable being fixed to a fixation point located in the proximal region of said housing, said fixation point being fixed with respect to said housing during injection, and the distal end of said rigid cable being slidingly received within said hollow cylinder, said distal end of said rigid cable being provided with a projection having an external diameter greater than the internal diameter of said collar, the length of said rigid cable being less than the distance separating said collar of said piston rod from said fixation point at the end of injection, the distal movement of said piston rod under the effect of said biasing means causing said rigid cable to break at the end of injection.

5. The device according to claim 4, wherein said rigid cable is made of polypropylene.

\* \* \* \* \*